United States Patent [19]

DeGonia et al.

[11] Patent Number: 5,071,919
[45] Date of Patent: Dec. 10, 1991

[54] SUBSTITUTED ACYLATING AGENTS AND THEIR PRODUCTION

[75] Inventors: David J. DeGonia, Granite City; Paul G. Griffin, Collinsville, both of Ill.

[73] Assignee: Ethyl Petroleum Additives, Inc., St. Louis, Mo.

[21] Appl. No.: 524,422

[22] Filed: May 17, 1990

[51] Int. Cl.$^5$ .......................................... C08F 138/00
[52] U.S. Cl. .................................. 525/285; 525/301; 525/333.7; 525/386
[58] Field of Search .............................. 525/285, 301

[56] References Cited

U.S. PATENT DOCUMENTS

| | | | |
|---|---|---|---|
| 3,215,707 | 11/1965 | Rense | 260/326.3 |
| 3,231,587 | 1/1966 | Rense | 260/346.8 |
| 3,382,172 | 5/1968 | Lowe | 252/42.7 |
| 3,476,774 | 11/1969 | Zaweski et al. | 260/346.8 |
| 4,152,499 | 5/1979 | Boerzel et al. | 526/52.4 |
| 4,234,435 | 11/1980 | Meinhardt et al. | 252/51.5 |
| 4,235,786 | 1/1980 | Wisotsky | 260/346.74 |
| 4,736,044 | 4/1988 | Hansen | 549/255 |
| 4,761,488 | 8/1988 | Fried | 549/255 |
| 4,883,886 | 11/1989 | Huang | 549/255 |
| 4,956,478 | 9/1990 | Fakoukakis et al. | 549/255 |

FOREIGN PATENT DOCUMENTS

| | | |
|---|---|---|
| 0317004 | 5/1989 | European Pat. Off. . |
| 0355895 | 2/1990 | European Pat. Off. . |
| 2904314 | 8/1980 | Fed. Rep. of Germany . |
| 579283 | 11/1977 | U.S.S.R. . |

*Primary Examiner*—Bernard Lipman
*Attorney, Agent, or Firm*—J. F. Sieberth; David E. LaRose

[57] ABSTRACT

Polybutenyl substituted succinic acylating agents are formed by reacting (a) an acidic reactant represented by the general formula

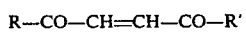

wherein R and R' are independently —OH, —O-lower alkyl, a halogen atom, or taken together are a single oxygen atom, with (b) a polymer composed mainly or entirely of polyisobutene, at least 50% of the polyisobutene content of the polymer having an end group represented by the formula

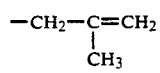

The mole ratio of acidic reactant:polymer is at least 1:1; and the reaction mixture is maintained under superatmospheric pressure during at least a substantial portion of the reaction period. The reaction rate is high, the yields of desired product are high, and despite the fact that superatmospheric pressures and elevated temperatures are used, the process forms only small amounts of tars or resinous co-products, even when employing as much as a 20% or more molar excess of maleic anhydride. Any unreacted acidic reactant such as maleic anhydride, maleic acid, fumaric acid, etc, can be, and preferably is, recovered from the reaction mixture, and thus is available for use either as recycle to the process or for other uses. Inasmuch as chlorine is not used in the process, the expense and difficulties associated with handling chlorine on a plant scale are eliminated, and the product is less corrosive than corresponding products formed by use of chlorine.

50 Claims, No Drawings

SUBSTITUTED ACYLATING AGENTS AND THEIR PRODUCTION

Technical Field

This invention relates to novel and eminently useful substituted acylating agents of the polybutenylsuccinic acid type, and to novel and eminently useful methods for their production.

Background

Heretofore processes have been described for the thermal reaction between polybutenes (predominantly polyisobutenes) and maleic anhydride or like reactants whereby polybutenyl succinic anhydrides are formed. Some of the work along these lines is described, or at least referred to, for example in U.S. Pat. Nos. 3,018,247; 3,018,250; 3,018,291; 3,172,892; 3,184,474; 3,185,704; 3,194,812; 3,194,814; 3,202,678; 3,216,936; 3,219,666; 3,272,746; 3,287,271; 3,311,558; and in British Pat. No. 1 492 337. However as pointed out in U.S. Pat. Nos. 3,215,707 and 3,231,587, from the standpoint of commercial usefulness the alkylation of maleic anhydride with an olefinic hydrocarbon is very time-consuming and limited in its applicability to relatively low molecular weight olefinic hydrocarbon reactants, i.e., those having less than about 12–15 carbon atoms. These two patents further state that the higher molecular weight olefinic hydrocarbons are apparently not sufficiently reactive with maleic anhydride to be useful as an alkylating agent, and that higher molecular weight hydrocarbon-substituted succinic acid compounds are almost invariably prepared by reacting maleic anhydride with a halogenated high molecular weight hydrocarbon reactant. Indeed, in U.S. No. 4,234,435 it is reported that the process as described in these two patents is presently deemed best for preparing the substituted succinic acylating agents.

British Pat. No. 1 492 337 points out that while such acylating agents can be prepared by thermally reacting a polymer having an average molecular weight above about 200 with maleic anhydride at a temperature above 200° C., the reaction rate of such reactions is low and that attempts to improve the reaction rate by increasing the temperature and/or by using superatmospheric pressure results in degradation of maleic anhydride to useless carbon dioxide, water and tarry solids.

U.S. Pat. No. 3,476,774 reports in Example 1 that reaction under nitrogen between polybutene and maleic anhydride conducted in a pressure vessel at 234° C.–236° C. for 6 hours and 40 minutes in o-dichlorobenzene solvent gave an alkenyl succinic anhydride product that had particles of sludge suspended in it. Improvements in yield are reported in Examples 2–4 of the patent wherein a thermal stabilizer (4,4'-methylenebis(2,6-di-tert-butyl-phenol)) was incorporated in the reaction mixture.

U.S. Pat. No. 4,883,886, in discussing the addition reaction between viscous polyalkenes and anhydride reactants such as maleic anhydride, states that a known problem frequently encountered in this reaction is thermal decomposition and polymerization of the unsaturated anhydride reactant at temperatures above about 150° C. According to the patentee, such thermal decomposition is accompanied by evolution of water vapor and oxides of carbon, and in a closed reaction vessel is accompanied by an increase in internal pressure. The patentee continues:

"Under some observed conditions, the thermal decomposition can be so rapid as to be explosive. In the absence of explosive thermal decomposition, a carbon-containing tarry residue is also formed in addition to water vapor and oxides of carbon. * * * Such thermal decomposition and attendant isomerization or polymerization of the unsaturated anhydride reactant has been observed as occuring during its addition reaction with polymeric olefins, e.g., polybutenes and others, in a closed reaction vessel. The carbon-containing residue varies in nature from somewhat granular when the decomposition is only slight to a tarry material mainly adhering to internal surfaces of the reaction vessel when the decomposition is more extensive but well below explosive magnitude. The granular type residue amounts to about from 0.1 to about 0.3 weight percent of the total charge and is generally dispersed in the alkenyl-substituted saturated anhydride addition compound product diluted with unreacted components of the olefin polymer, and is readily separated therefrom by filtration. However, the tarry residue product, which for the most part fouls the internals of the reaction vessel can be as high as 2–3 weight percent of the total charge. The tarry material not adhering to the internal surfaces of the reactor fouls the filter and interferes with filtration of the desired reaction product. Both types of residue are undesirable because of the above noted fouling characteristics and because their formation results in yield reduction of the desired alkenyl-substituted anhydride addition product."

The patentee refers to a number of other patents describing catalysts or agents which decrease such unwanted by-product formation, and utilizes such materials in a particular process in order to suppress the formation of tars and undesired side products.

U.S. Pat. No. 4,152,499 discloses that polybutenes having a higher proportion of terminal double bonds than conventional polybutenes can be produced by polymerizing isobutene with boron trifluoride as the intitiator, if (a) the polymerization is carried out at −50° C. to +30° C., (b) from 1 to 20 mmoles of boron trifluoride are used per mole of isobutene, and (c) the means polymerization time is confined to from 1 to 10 minutes. The patent further discloses that suchpolybutenes can be reacted with the stoichiometric amount of amleic anhydride, or a slight excess thereof, "in the ocnentional manner" at from 170° C. to 250° C., and that such polybutenes when head with maleci anhydride for 4 hours at 200° C. with stirring, followed by removing excess maleic anhydride under greatly reduced pressure exhibited a substantially greater activity than two commercial isobutene polymers. W. German Offenlegungsschrift 29 04 314 teaches the desirability of conducting the polymerization of the isobutene in the same manner except using a polymerization time limited to 1 to 40 seconds, and that to prepare mineral oil additives, "the polyisobutenes is reacted in known fashion with the stoichiometric amount or a slight excess of maleic acid anhydride at 170 to 250° C.

It has also been disclosed heretofore that a specified thermal maleinisation reaction can be used to assess the quality (reactivity) of a polybutene polymer. In this procedure polybutene (50g) is reacted with maleic anhydride (9.8g), a 1:2 mole ratio, for 24 hours in a stirred reaction tube immersed in a bath of specified hydrocarbons under reflux at 210° C. The reaction is conducted under nitrogen, and the reaction mixture is stirred at a specified number of revolutions per minute. A specifically designed apparatus is suggested for use in this procedure. The procedure results in the formation of both polybutenyl succinic anhydride and a complex resinous co-product formed from maleic anhydride.

The Invention

It has been found that substantial advantages can be realized by reacting an acidic reactant, such as maleic anhydride, with a substantially aliphatic polymer comprised principally or entirely of polyisobutenes in a mole ratio of acidic reactant(s) : polymer is at least 1 : 1, provided that at least 50% (preferably at least 75%) of the polyisobutenes content of such polymer has an end group represented by the formula

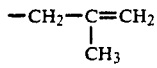

and the reaction mixture is maintained under superatmospheric pressure during at least a substantial portion of the reaction period. Most preferably, the polymer consists essentially of polyisobutenes (i.e., it contains at least 50 mole % and more preferably at least 60 mole % of polymerized isobutene) and at least 50% (more desirably at least 75%) of the total polymer(s) is polyisobutenes having such end group.

In order to determine in any given polyisobutenes the proportion thereof that contains the above identified end group, use can be made of Infra-Red Spectroscopy and, more preferably, $C_{13}$ Nuclear Magnetic Resonance. In $C_{13}$ NMR, typical olefin chemical shifts appear between 100 and 160 ppm. Structural identification can be confirmed by comparison with $C_{13}$ spectra of known olefins. See for example, *Atlas of Carbon-13 NMR Data*, edited by E. Breitmaier, G. Haas and W. Voelter, Spectra numbers 30–107. Quantitation can be accomplished by suppression of the NOE produced by proton attachment to carbon. Sufficient delay time is allowed for complete carbon relaxation.

Preferably, the entire reaction or substantially the entire reaction is conducted under superatmospheric pressure, such as by conducting the entire reaction or substantially the entire reaction in a closed reaction system at superatmospheric pressure. Most preferably, the process is conducted such that the superatmospheric pressure on the reaction mixture decreases after passing through an initial peak pressure, and then increases to another elevated pressure, especially where the latter elevated pressure is higher than the initial peak pressure.

For best results, (a) at least a substantial portion of the reaction is conducted at a pressure in the range of about 1 to about 75 psig or more (and preferably in the range of about 4 to about 50 psig), (b) the temperature of the reaction mixture is maintained in the range of about 220 to about 265° C. throughout substantially the entire reaction period, and (c) the mole ratio of the acidic reactant(s) : the polymer(s) is in the range of 1.1 1 to about 3 : 1, and preferably in the range of 1.1 : 1 to 1.9 1. It is to be understood however that departures from the foregoing ranges of pressure, temperature and/or proportions may be utilized in any given situation where such departure is deemed desirable under the given circumstances involved. All that is required in the practice of this invention is that the reaction be conducted under reaction conditions, including superatmospheric pressure, that enable the reaction to proceed without encountering excessive decomposition or excessive by-product formation (e.g., excessive tar or polymer formation).

It is particularly preferred to employ the reactants in mole ratios of acidic reactant to polyisobutenes such that the product contains an average molar ratio of succinic groups to polyisobutenes chains below 1.3 : 1.

Preferred acidic reactants that can be used in the process are those represented by the general formula

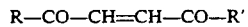

wherein R and R' are independently —OH, —O—lower alkyl, a halogen atom, or taken together are a single oxygen atom. Thus use can be made of such compounds as maleic acid, fumaric acid, the lower alkyl ($C_{1-7}$) esters of such acids, the acid halides (preferably the acid fluorides or chlorides) of such acids, maleic anhydride, or mixtures of any two or more of any such compounds. Other similar compounds which can be used are itaconic acid, itaconic anhydride, citraconic acid, citraconic anhydride, mesaconic acid, the lower alkyl esters and the acid halides of such acids, and the like. Maleic anhydride is the most preferred reactant for use in the process.

Among the advantages of this invention is that the reaction rate is high, the yields of desired product are high, and despite the fact that superatmospheric pressures and substantially elevated temperatures are used, the process forms only small amounts of tars or resinous co-products, even when employing as much as a 20% or more molar excess of maleic anhydride. Indeed, any unreacted acidic reactant such as maleic anhydride, maleic acid, fumaric acid, or the like can be, and preferably is, recovered from the reaction mixture, and thus is available for use either as recycle to the process or for other uses. Moreover, inasmuch as chlorine is not used in the process, the expense and difficulties associated with handling chlorine on a plant scale are eliminated, and the product is less corrosive than corresponding products formed by use of chlorine.

Another advantage of this invention is that thermal stabilizers or other additive materials to reduce tar formation are not required. Indeed, many of the known materials to reduce tar formation are halogen-containing substances (see for example U.S. Pat. Nos. 3,927,041; 3,935,249; 3,953,475; 3,954,812; 3,960,900; 3,985,672; 4,008,168; 4,086,251; 4,414,397; 4,434,071; and 4,496,746). Halogen-containing components are generally undesirable because they tend to leave halogen-containing residues in the product.

Thus products with almost no tarry co-products or halogen-containing residues can be formed in exceptionally high yields in the process of this invention without use of such extraneous materials as thermal stabilizers and tar suppressors which add to the cost of the operation and can leave undesirable impurities in the product. In fact, it has been found possible to achieve higher conversions of maleic anhydride to alkenyl succinic anhydride by use of the process of this invention without a thermal stabilizer than the conversions reported in U.S. Pat. No. 3,476,774 (Examples 2–4) wherein a thermal stabilizer was used. For example, the yields based on conversion of maleic anhydride to the desired product reported in Examples 2–4 of the patent average 80%. In contrast, a group of 8 runs pursuant to this invention conducted in Examples 6–8 presented hereinafter give a conversion on the same basis averaging 92%.

The polybutenes or like polymers utilized in the practice of this invention may have number average molecular weights in the range of 500 to 100,000 or more. The preferred polymers are those having number average molecular weights in the range of 700 to 5,000, and the most preferred polymers are those having number average molecular weights in the range of 800 to 1,300.

If desired, the reaction can be conducted in an inert liquid reaction medium or diluent such as one or more saturated aliphatic, saturated cycloaliphatic, or aromatic hydrocarbons, e.g., mineral oil, etc. Preferably, however, the reaction is conducted in the absence of an ancillary reaction solvent or diluent. A small amount of catalyst such as aluminum trichloride, triethylaluminum, methylaluminum sesquichloride, diethylaluminum chloride, or the like, may be employed in heprocess.

The practice and advantages of this invention will become still further apparent from eh following illustrative examples, which are not intended to limit, and should not be construed as limiting, the scope of this invention.

In these examples all parts and percentages are by weight unless otherwise specified. also the "cook period" referred to in the examples is designated as the point where the reaction mass reaches its specified reaction temperature, and thus at this point the cook time is equal to 0. The polybutene used in Examples 1-6 was a substantial pure polyisobutyleen with a weight average molecular weight of about 9995. approximately 78% of the polymer had an end group as depicted in Formula I above. In Examples 6-8 the polybutene employed was a substantially pure polyisobutylene with a weight average molecular weight of about 1300. This polybutene also contained about 78% of polymer having the above-depicted end group. Conventional commercially-available polyisobutenes contains less than about 10% of polymer containing such end group.

EXAMPLE 1

Into an autoclave were charged 1200 parts of polybutene (PIB), 130.7 parts of maleic anhydride (MA) and 0.12 part of aluminum trichloride. The mole ratio of MA:PIB was thus 1:1. A vacuum (-26 inches of water) was applied to the autoclave for 10 minutes to remove the oxygen (air), and while holding the system under a low vacuum the autoclave was heated. When the autoclave temperature reached 90° C., the agitator was turned on. When the temperature reached 225° C., the pressure within the autoclave was 12.5 psig. Thereupon the reaction mixture was kept at 225° C. for 5 hours while continuously agitating the reaction mixture. The pressure profile on the reaction mass during this period was as follows:

| Cook Time, minutes | Pressure, psig |
| --- | --- |
| 0 | 12.5 |
| 5 | 13.0 |
| 15 | 8.0 |
| 25 | 5.0 |
| 40 | 4.5 |
| 50 | 3.5 |
| 65 | 2.0 |
| 80 | 1.0 |
| 95 | 0.5 |
| 135 | 0 |
| 150 | −0.5 |
| 170 | 0 |
| 185 | 0.5 |
| 210 | 1.5 |
| 235 | 3.0 |
| 255 | 4.0 |
| 300 | 6.0 |

The resultant reaction product was subjected to vacuum stripping to remove volatiles (primarily unreacted maleic anhydride). The polybuteneyl succinic anhydride reaction product had an acid number before stripping of 0.92, and an acid number after stripping of 0.76.

EXAMPLE 2

The general procedure of Example 1 was repeated, the chief difference being that the reactants were kept at 240° C. during the major portion of the reaction period. The pressure profile on the reaction mass during the reaction was as follows:

| Cook Time, minutes | Pressure, psig |
| --- | --- |
| 0 | 17.0 |
| 5 | 14.0 |
| 25 | 6.0 |
| 35 | 4.5 |
| 45 | 3.0 |
| 55 | 2.5 |
| 75 | 2.0 |
| 90 | 2.0 |
| 105 | 2.0 |
| 135 | 3.5 |
| 170 | 5.0 |
| 205 | 5.0 |
| 250 | 6.0 |
| 300 | 7.0 |

The resultant reaction product was subjected to vacuum stripping to remove volatiles (primarily unreacted maleic anhydride). The polybuteneyl succinic anhydride reaction product had an acid number before stripping of 0.92, and an acid number after stripping of 0.82.

EXAMPLE 3

Using the same reactants and the same general procedure as in Example 1, the reactants were employed in a MA:PIB mole ratio of 1.1:1 (143.8 parts of MA and 1200 parts of PIB). The pressure profile on the reaction mass during the reaction at 225° C. was as follows:

| Cook Time, minutes | Pressure, psig |
| --- | --- |
| 0 | 12.0 |
| 5 | 14.5 |
| 10 | 12.0 |
| 30 | 6.0 |
| 60 | 3.5 |
| 90 | 2.0 |
| 120 | 1.0 |
| 150 | 1.0 |
| 180 | 1.0 |
| 210 | 1.0 |
| 240 | 1.5 |
| 270 | 3.0 |
| 300 | 4.5 |

The polybuteneyl succinic anhydride reaction product had an acid number before vacuum stripping of 1.04, and an acid number after stripping of 0.81.

EXAMPLE 4

In this run the same reactants as in Example 1 were reactant 240° C. at a mole ratio (MA:PIB) of 1.1:1. the pressure profile on the reaction mass during the reaction was as follows:

| Cook Time, minutes | Pressure, psig |
| --- | --- |
| 0 | 17.0 |
| 10 | 15.0 |
| 25 | 10.0 |
| 30 | 9.0 |
| 45 | 7.5 |
| 55 | 7.0 |
| 65 | 6.0 |
| 80 | 5.5 |
| 95 | 6.0 |
| 115 | 6.0 |
| 135 | 8.5 |
| 155 | 10.0 |
| 180 | 13.5 |
| 195 | 16.0 |
| 215 | 19.0 |
| 235 | 22.5 |
| 250 | 25.5 |
| 265 | 28.0 |
| 280 | 31.5 |
| 300 | 34.0 |

The acid number of the polybuteneyl succinic anhydride reaction product before vacuum stripping was 1.02. After stripping the product had an acid number of 0.91.

EXAMPLE 5

The same reactants as in Example 1 were reacted at 240° C. at a mole ratio (MA:PIB) of 1.2:1 (155.65 parts of MA and 1190 parts of PIB). The pressure profile on the reaction mass during the reaction was as follows:

| Cook Time, minutes | Pressure, psig |
| --- | --- |
| 0 | 18.0 |
| 5 | 17.5 |
| 35 | 7.0 |
| 60 | 5.0 |
| 90 | 4.5 |
| 120 | 5.0 |
| 150 | 6.0 |
| 180 | 7.0 |
| 210 | 10.0 |
| 240 | 13.5 |
| 270 | 17.0 |
| 300 | 21.0 |

The acid numbers of the polybutenyl succinic anhydride reaction product were 1.09 before stripping, and 0.95 after stripping.

EXAMPLE 6

Into an autoclave were charged 1211.8 parts of polybutene (PIB), 118.9 parts of maleic anhydride (MA) and 0.12 part of aluminum trichloride. The mole ratio of MA:PIB was thus 1.3:1. A vacuum (−26 inches of water) was applied to the autoclave for 10 minutes to remove the oxygen (air), and while holding the system under a low vacuum the autoclave was heated. When the autoclave temperature reached 105° C., the agitator was turned on. When the temperature reached 240° C., the pressure within the autoclave was 17.0 psig. Thereupon the reaction mixture was kept at 240° C. for 5 hours while continuously agitating the reaction mixture. The pressure profile on the reaction mass during this period was as follows:

| Cook Time, minutes | Pressure, psig |
| --- | --- |
| 0 | 17.0 |
| 15 | 14.0 |
| 30 | 10.5 |
| 45 | 8.0 |
| 70 | 6.5 |
| 95 | 6.5 |
| 115 | 8.0 |
| 150 | 12.0 |
| 195 | 19.0 |
| 230 | 26.0 |
| 260 | 33.0 |
| 300 | 40.5 |

The reaction product was subjected to vacuum stripping o remove volatiles (primarily unreacted maleic anhydride). The acid numbers o the polybuteneyl succinic anhydride reaction product were 0.84 before stripping, and 0.78 after stripping.

EXAMPLE 7

The same reactants as in Example 6 were reacted in the same general manner at 240° C. at a mole ratio (MA:PIB) of 1.5:1 (135.3 paets of MA and 1195.4 parts of PIB). The pressure profile on the reaction mass during the reaction was as follows:

| Cook Time, minutes | Pressure, psig |
| --- | --- |
| 0 | 15.5 |
| 5 | 16.0 |
| 20 | 12.5 |
| 40 | 10.0 |
| 45 | 9.5 |
| 60 | 8.5 |
| 80 | 8.5 |
| 110 | 10.0 |
| 140 | 14.0 |
| 180 | 20.5 |
| 205 | 26.5 |
| 245 | 37.0 |
| 255 | 40.0 |
| 270 | 43.0 |
| 300 | 50.0 |

The acid numbers of the polybutenyl succinic anhydride reaction product were 0.91 before stripping, and 0.83 after stripping.

Table 1 summarizes the total tar content and the strip acid number of the respective products of Examples 1-5, and provides a comparison of the corresponding values on a product made under the same general reaction conditions (including superatmospheric pressure) using a PIB that contained less than 10% of above-depicted end group, and wherein the mole ratio (MA:PIB) was 1:1.

The procedure for determination of total tar content used herein was as follows: After completion of the reaction run, the reactor head and attached agitator are removed, and the reactor contents are transferred from the autoclave to storage and analysis bottles. The appearance of the reactor and its component parts is immediately rated by at least two, and preferably three, trained technical personnel. The rating takes place in a specific manner, namely:

1) Each of the three major internal components of the autoclave—i.e., the sides, the bottom, and the agitator, is independently rated.

2) The rating is based upon the visual appearance of the component and the amount of tar present. The rating scale ranges from 1 to 10, with "1" representing a perfectly clean component showing no evidence of tar formation. The rating of "10" represents a heavily tarred component which is completely covered with tar. In general, an intermediate rating corresponds to the area of the surface covered by the black tar. For example, a rating of "7" means that approximately 70% of the surface is covered with tar.

3) Each person making the evaluations works independently of the other person(s) and thus records his/her observations without consultation with, or knowledge of the ratings made by, the other person(s).

4) The rating numbers for the three individual components are added together for each individual evaluator and the sum of all of these totals are averaged (i.e., divided by the number of evaluators) to yield an average total tar rating reported herein.

5) The average total tar rating scale is as follows:
3 to 5 —Excellent; very clean reactor, tar formation minimal or non-existent
6 to 10 —Good; some tar formation
11 to 14 —Fair; significant level of tar formation
15 to 20 —Poor; medium to heavy tar formation
20 to 30 —Very Poor; heavy to severe tar formation

TABLE 1

Key Properties of Polyisobutenyl Succinic Anhydrides

| Example | Reaction Temperature | MA:PIB Ratio | Maximum Pressure | Total Tars | Strip Acid No. |
|---------|---------------------|--------------|------------------|------------|----------------|
| 1 | 225° C. | 1.00 | 13.0 psig | 4 | 0.76 |
| 2 | 240° C. | 1.00 | 17.0 psig | 4 | 0.82 |
| 3 | 225° C. | 1.10 | 14.5 psig | 3 | 0.81 |
| 4 | 240° C. | 1.10 | 34.0 psig | 3 | 0.90 |
| 5 | 240° C. | 1.20 | 21.0 psig | 3 | 0.95 |
| Control | 225° C. | 1.00 | 15.0 psig | 7 | 0.60 |

EXAMPLE 8

The same reactants as in Example 6 were reacted in the same general manner at 240° C. at a mole ratio (MA:PIB) of 12.3:1 (118.9 parts of MA and 1211.8 parts of PIB) except that the aluminum chloride catalyst was not used. Agitation of the reactants was commenced when the temperature reached 60° C. The pressure profile on the reaction mass during the reaction was as follows:

| Cook Time, minutes | Pressure, psig |
|--------------------|----------------|
| 0 | 16.5 |
| 10 | 11.5 |
| 35 | 7.0 |
| 50 | 6.0 |
| 75 | 6.0 |
| 100 | 7.0 |
| 130 | 9.0 |
| 165 | 11.5 |
| 195 | 14.5 |
| 240 | 20.0 |
| 260 | 22.0 |
| 280 | 25.0 |
| 300 | 27.0 |

The acid number of the polybutenyl succinic anhydride reaction product before stripping was 0.84, and after stripping, 0.77. Average total tars was 4.

EXAMPLE 9

This example demonstrates that unreacted maleic anhydride can be recovered from the reaction mixture and recycled for use in subsequent runs. In particular, an initial batch run was made followed by two recycle batch runs in which the maleic anhydride from the prior run was used as part of the total maleic anhydride charge. In this series of runs the same reactants as in Example 6 were used. The charges to the reactor were:

Run 1 —MA, 118.9 parts; PIB, 1211.8 parts; AlCl$_3$, 0.12 part.

Run 2 —Fresh MA, 107.6 parts, recycled MA, 11.7 parts; PIB, 1211.8 parts; AlCl$_3$, 0.12 part.

Run 3 —Fresh MA, 106.4 parts, recycled MA, 12.5 parts; PIB, 1211.8 parts; AlCl$_3$, 0.12 part.

Agitation of the reactants was commenced when the temperature reached 60°-70° C. The pressure profile on the reaction mass during the reaction was as follows:

| Run 1 | | Run 2 | | Run 3 | |
|---|---|---|---|---|---|
| Cook Time minutes | Pressure psig | Cook Time minutes | Pressure psig | Cook Time minutes | Pressure psig |
| 0 | 19.0 | 0 | 20.0 | 0 | 16.0 |
| 10 | 14.5 | 10 | 16.0 | 10 | 14.0 |
| 25 | 9.5 | 25 | 9.0 | 20 | 9.5 |
| 35 | 8.0 | 40 | 7.5 | 40 | 7.0 |
| 60 | 5.5 | 65 | 5.0 | 55 | 5.0 |
| 95 | 5.5 | 85 | 5.0 | 85 | 5.0 |
| 130 | 7.5 | 120 | 6.0 | 100 | 5.0 |
| 150 | 9.0 | 155 | 9.0 | 120 | 5.0 |
| 180 | 12.0 | 175 | 11.5 | 170 | 9.0 |
| 225 | 19.0 | 215 | 17.0 | 200 | 11.0 |
| 255 | 23.0 | 240 | 21.0 | 230 | 16.0 |
| 260 | 28.0 | 260 | 23.5 | 285 | 23.5 |
| 300 | 30.0 | 280 | 27.0 | 300 | 25.0 |
| | | 300 | 30.0 | | |

Table 2 includes a summary of the results of this series of runs.

TABLE 2

Highlights of Recycle Process

| Run No. | % MA Recycled | Total Tars | Stripped Acid No. | Unreacted PIB, % |
|---------|---------------|------------|-------------------|------------------|
| 1 | None | 3 | 0.75 | 27.2 |
| 2 | 9.8 | 3 | 0.73 | 24.0 |
| 3 | 10.5 | 3 | 0.73 | 24.2 |

EXAMPLE 10

The procedure of Example 4 was repeated yielding the following pressure profile:

| Cook Time, minutes | Pressure, psig |
|--------------------|----------------|
| 0 | 17.0 |
| 10 | 15.0 |
| 25 | 10.0 |
| 30 | 9.0 |
| 45 | 7.5 |
| 55 | 7.0 |
| 65 | 6.0 |
| 80 | 5.5 |
| 95 | 6.0 |
| 115 | 6.0 |
| 135 | 8.5 |
| 155 | 10.0 |
| 180 | 13.5 |
| 195 | 16.0 |
| 215 | 19.0 |
| 235 | 22.5 |

| Cook Time, minutes | Pressure, psig |
| --- | --- |
| 250 | 25.5 |
| 265 | 28.0 |
| 280 | 31.5 |
| 300 | 34.0 |

The reaction mixture before stripping had a total tar content of 3. The acid number of the polybuteneyl succinic anhydride product after vacuum stripping was 0.91.

The reaction product mixtures formed in the process of this invention are of particular advantage in that they contain little or no tars; they usually give a rating by the above procedure of 3 or 4. thus the interior surfaces of the reactor are free or essentially free of tars or other resinous coatings, and moreover the effective utilization of the raw materials used in the process is high. Moreover, after removal of residual unreacted acidic reactant (i.e., the maleic anhydride or like carboxylic reactant) charged to the reactor (if any remains unreacted) such as by distillation or stripping at reduced pressure, the remainder of the product generally will have an acid number of at least 0.7, preferably at least 0.8, and in the most preferred cases, at least 0.9. Such product can be used without further treatment or purification either as an additive or as a raw material for use in the production of dispersant additives.

The polybutenyl succinic acids or acid derivatives thereof (polybutenyl succinic anhydrides, polybutenyl succinic acid halides, polybutenyl succinic acid lower alkyl esters) are useful as corrosion inhibitors for liquid fuels such as gasoline and middle distillate fuels (diesel fuel, burner fuel, turbine fuel, jet fuel, kerosene, etc.). In addition they are especially useful in the manufacture of polybutenyl succinic acid esters and polybutenyl succinimides by reaction with alcohols or amines, preferably alkylene polyamines such as ethylene or propylene diamines, diethylene triamine, triethylene tetramine, tetraethylene pentamine, pentaethylene hexamine, etc. Such polybutenyl succinic acid esters and polybutenyl succinimides are especially useful as ashless dispersants in lubricating oils and functional fluids.

Methods for producing polybutenes useful in the practice of this invention are described in U.S. Pat. No. 4,152,499 and in W. German Offenlegungsschrift 29 04 314, the disclosures of which are incorporated herein by reference. Suitable products are understood to be available under the trade designation "Ultravis".

While this invention has been discussed with reference to use of polybutenes as the polyolefin reactant, use can be made of other polyolefins having an end group configuration comparable to that depicted hereinabove, such as isopentene polymers, isohexene polymers, isobutene-propylene copolymers, isobutene-ethylene copolymers, isobutene-ethylene-propylene terpolymers, isobutene-amylene copolymers, and the like.

This invention is susceptible to considerable variation in its practice within the spirit and scope of the ensuing claims, the forms hereinbefore described constituting preferred embodiments thereof.

What is claimed is:

1. A process for preparing substituted succinic acylating agents which comprises reacting (i) at least one substantially aliphatic polymer of at least one lower olefin, and (ii) an acidic reactant or a mixture of two or more acidic reactants represented by the general formula

R—CO—CH=CH—CO—R' wherein R and R' are independently —OH,—O—lower alkyl, a halogen atom, or taken together are a single oxygen atom; the process being characterized in that:
a) the substantially aliphatic polymer is comprised predominantly or entirely of polyisobutenes, at least 50% of the polyisoutene content of such polymer having an end group represented by the formula $$-CH_2-\underset{\underset{CH_3}{|}}{C}=CH_2$$

b) the mole ratio of aid acidic reactant(s): said polymer(s) is at least 1:1;
c) the reaction mixture is maintained under superatmospheric pressure during at least a substantial portion of the reaction period; and
d) said acylating agent is characterized by having a average total tars value as determined by the method described in the specification hereof of less than 5.

2. A process as claimed in claim 1 wherein the acidic reactant consists essentially of maleic anhydride.

3. A process as claimed in claim 1 wherein the polymer consists essentially of polyisobutenes and at least 50% of the total polymer(s) is polyisobutenes having said end group.

4. A process as claimed in claim 1 wherein the polymer consists essentially of polyisobutenes and at least 75% of such polymer has said end group.

5. A process as claimed in claim 1 wherein the entire reaction or substantially the entire reaction is conducted under superatmospheric pressure.

6. A process as claimed in claim 1 wherein the entire reaction or substantially the entire reaction is conducted in.a closed reaction system at superatmospheric pressure.

7. A process as claimed in claim 1 conducted such that the superatmospheric pressure on the reaction mixture decreases after passing through an initial peak pressure, and then increases to another elevated pressure.

8. A process as claimed in claim 7 wherein such elevated pressure is higher than the initial peak pressure.

9. A process as claimed in claim 1 wherein at least a substantial portion of the reaction is conducted at a pressure in the range of about 4 to about 50 psig.

10. A process as claimed in claim 1 wherein the temperature of the reaction mixture is maintained in the range of about 220° to about 265° C. throughout substantially the entire reaction period.

11. A process as claimed in claim 1 wherein the mole ratio of said acidic reactant(s) : said polymer(s) is in the range of 1.1 1 to about 1.9 : 1.

12. A process as claimed in claim 1 wherein the mole ratio of said acidic reactant(s) : said polymer(s) is in the range of 1.1 1 to about 1.9 : 1, and wherein unreacted acidic reactant is recovered from the reaction mixture.

13. A process as claimed in claim 1 wherein the mole ratio of said acidic reactant(s) : said polymer(s) is such that the product contains in chemically combined. form an average of less than 1.3 moles of acid groups per mole of polymer chains chemically combined therewith.

14. A process as claimed in claim 1 wherein the acidic reactant consists essentially of maleic anhydride, wherein the mole ratio of maleic anhydride : said polymer(s) is in the range of 1.1 : 1 to.1.9 : 1, and wherein unreacted maleic anhydride is recovered from the reaction mixture.

15. A process as claimed in claim 1 wherein the acidic reactant consists essentially of maleic anhydride and wherein the polymer consists essentially of polyisobutenes. of the polymer has said end group.

16. A process as claimed in claim 15 wherein at least 75% of the polymer has said end group.

17. A process as claimed in claim 16 wherein the entire reaction or substantially the entire reaction is conducted in a closed reaction system at superatmospheric pressure.

18. A process as claimed in claim 17 conducted such that the superatmospheric pressure on the reaction mixture decreases after passing through an initial peak pressure, and then increases to another elevated pressure.

19. A process as claimed in claim 18 wherein such elevated pressure is higher than the initial peak pressure.

20. A process as claimed in claim 15 wherein at least a substantial portion of the reaction is conducted at a pressure in the range of about 4 to about 50 psig.

21. A process as claimed in claim 15 wherein the temperature of the reaction mixture is maintained in the range of about 220° to about 265° C. throughout substantially the entire reaction period.

22. A process as claimed in claim 15 wherein the mole ratio of maleic anhydride : polyisobutenes is in the range of 1.1 1 to about 1.9 : 1.

23. A process as claimed in claim 16 wherein at least 75% of the polymer has said end group, wherein the entire reaction or substantially the entire reaction is conducted in a closed reaction system at superatmospheric pressure, and wherein the temperature of the reaction mixture is maintained in the range of about 220° to about 265° C. throughout substantially the entire reaction period.

24. A process as claimed in claim 23 conducted such that the superatmospheric pressure on the reaction mixture decreases after passing through an initial peak pressure, and then increases to another elevated pressure.

25. A process as claimed in claim 24 wherein such elevated pressure is higher than the initial peak pressure.

26. A process as claimed in claim 23 wherein at least a substantial portion of the reaction is conducted at a pressure in the range of about 4 to about 50 psig.

27. A process as claimed in claim 23 wherein the temperature of the reaction mixture is maintained in the range of about 220° to about 265° C. throughout substantially the entire reaction period.

28. A process as claimed in claim 23 wherein the mole ratio of maleic anhydride : polyisobutenes is in the range of 1.1 1 to about 1.9 :,1.

29. A process as claimed in claim 15 wherein at least 75% of the polymer has said end group, wherein the entire reaction or substantially the entire reaction is conducted in a closed reaction system at superatmospheric pressure, wherein the temperature of the reaction mixture is maintained in the range of about 220° to about 265° C. throughout substantially the entire reaction period, and wherein the reaction is conducted such that the superatmospheric pressure on the reaction mixture decreases after passing through an initial peak pressure, and then increases to another elevated pressure, such elevated pressure being higher than the initial peak pressure.

30. A process as claimed in claim 29 wherein the mole ratio of maleic anhydride : polyisobutenes is in the range of 1.1 1 to about 1.9 : 1, and wherein the temperature of the reaction mixture is maintained in the range of about 220° to about 265° C. throughout substantially the entire reaction period.

31. A process as claimed in claim 30 wherein unreacted maleic anhydride is recovered from the reaction mixture.

32. A process as claimed in claim 15 wherein the mole ratio of maleic anhydride to polyisobutenes is such that the product contains in chemically combined form an average of less than 1.3 moles of succinic groups per mole of polymer chains chemically combined therewith.

33. A product formed by the process of claim 1.

34. A product formed by the process of claim 1, said product being characterized by having a average total tars value as determined by the method described in the specification hereof of less than 5.

35. A product formed by the process of claim 1, said product being characterized by containing in chemically combined form an average of less than 1.3 moles of succinic groups per mole of polymer chains chemically combined therewith.

36. A product formed by the process of claim 11.

37. A product formed by the process of claim 11, said product being characterized by containing in chemically combined form an average of less than 1.3 moles of succinic groups per mole of polymer chains chemically combined therewith.

38. A product formed by the process of claim 14, said product being characterized by having a average total tars value as determined by the method described in the specification hereof of less than 4.

39. A product formed in the process of claim 14, said product being characterized by having, after removal of residual acidic reactant or reactants an acid number of at least 0.7.

40. A composition as claimed in claim 39 wherein the acid number is at least 0.8.

41. A composition as claimed in claim 39 wherein the acid number is at least 0.9.

42. A product formed in the process of claim 14, said product being characterized (i) by having a average total tars value as determined by the method described in the specification hereof of less than 5, and (ii) by having, after removal of residual acidic reactant or reactants an acid number of at least 0.7.

43. A product formed in the process of claim 14, said product being characterized (i) by having a average total tars value as determined by the method described in the specification hereof of less than 4, and (ii) by having, after removal of residual acidic reactant or reactants an acid number of at least 0.8.

44. A composition as claimed in claim 43 wherein the acid number is at least 0.9.

45. A polybutenyl succinic anhydride reaction product formed from maleic anhydride and polybutene polymer comprised predominantly of polyisobutenes, said polymer having a number average molecular weight in the range of 500 to 10,000, at least 50% of the polyisobutenes content of such polymer having an end group represented by the formula $$-CH_2-\underset{\underset{CH_3}{|}}{C}=CH_2$$

said polybutenyl succinic anhydride product having a average total tars value as determined by the method described in the specification hereof of less than 5, and having, after removal of residual acidic reactant or reactants an acid number of at least 0.7.

46. A composition as claimed in claim 45 wherein the a number is at least 0.8.

47. A composition as claimed in claim 45 wherein the number is at least 0.9.

48. A composition as claimed in claim 45 wherein the polybutenyl succinic anhydride contains in chemically combined form an average of less than 1.3 moles of succinic groups per mole of polymer chains chemically combined therewith.

49. The process of claim 1 wherein the reaction of (i) and (ii) is conducted i the substantial absence of a thermal stabilizer.

50. The process of claim 31 wherein the reaction is conducted inthe substantial absence of a thermal stabilizer.

* * * * *